United States Patent
Freedman et al.

(10) Patent No.: US 12,420,115 B2
(45) Date of Patent: Sep. 23, 2025

(54) CHARACTERIZING PHYSICAL PROPERTIES OF AN ATTENUATING ELEMENT IN A RADIOTHERAPY DEVICE

(71) Applicant: Elekta Limited, Crawley (GB)

(72) Inventors: Joshua Freedman, Crawley (GB); David Roberts, Crawley (GB); Stefan Pencea, Decatur, GA (US)

(73) Assignee: Elekta Limited, Crawley (GB)

( * ) Notice: Subject to any disclaimer, the term of this patent is extended or adjusted under 35 U.S.C. 154(b) by 194 days.

(21) Appl. No.: 17/757,520

(22) PCT Filed: Dec. 16, 2020

(86) PCT No.: PCT/EP2020/086439
§ 371 (c)(1),
(2) Date: Jun. 16, 2022

(87) PCT Pub. No.: WO2021/122761
PCT Pub. Date: Jun. 24, 2021

(65) Prior Publication Data
US 2023/0028022 A1      Jan. 26, 2023

(30) Foreign Application Priority Data
Dec. 18, 2019   (GB) ..................................... 1918767

(51) Int. Cl.
*A61N 5/10*       (2006.01)
(52) U.S. Cl.
CPC .......... *A61N 5/1048* (2013.01); *A61N 5/1042* (2013.01)
(58) Field of Classification Search
None
See application file for complete search history.

(56) References Cited

U.S. PATENT DOCUMENTS 7,801,269 B2 *   9/2010   Cravens ............... A61N 5/1048
                                                                378/65
8,611,591 B2 *  12/2013   Coffman ................ G06T 7/277
                                                                382/104
(Continued)

FOREIGN PATENT DOCUMENTS

CN          105658278          6/2016
EP          2904974 A1         8/2015
(Continued)

OTHER PUBLICATIONS

"European Application No. 1918767.3, Search Report dated Jun. 29, 2020", (Jun. 29, 2020), 9 pgs.
(Continued)

*Primary Examiner* — David P Porta
*Assistant Examiner* — Djura Malevic
(74) *Attorney, Agent, or Firm* — Schwegman Lundberg & Woessner, P.A.

(57) ABSTRACT

Disclosed herein is a method of characterising physical properties of an attenuating element in a radiotherapy device having a radiotherapy radiation source and a radiotherapy radiation detector on respective sides of the attenuating element. The method comprises obtaining an average detected radiotherapy radiation intensity at two or more locations around the attenuating element, comparing the detected intensity at one location with the average intensity, and characterising a corresponding physical property based on the comparison.

16 Claims, 6 Drawing Sheets

(56) References Cited

U.S. PATENT DOCUMENTS

| | | | | |
|---|---|---|---|---|
| 8,797,030 | B2* | 8/2014 | Alagappan | G01R 33/34007 324/322 |
| 8,896,308 | B2* | 11/2014 | Shvartsman | G01R 33/385 324/309 |
| 9,265,971 | B2* | 2/2016 | Baltes | A61N 5/1048 |
| 10,132,888 | B2* | 11/2018 | Shvartsman | G01R 33/4808 |
| 10,206,650 | B2* | 2/2019 | Rozas | A61B 6/585 |
| 10,286,229 | B2* | 5/2019 | Baltes | A61N 5/1071 |
| 10,398,405 | B2* | 9/2019 | Rozas | G06T 11/005 |
| 10,434,338 | B2* | 10/2019 | Sayeed | A61N 5/1039 |
| 10,441,819 | B2* | 10/2019 | Sayeed | A61N 5/1071 |
| 10,553,313 | B2* | 2/2020 | Yaddanapudi | A61N 5/1075 |
| 10,682,527 | B2* | 6/2020 | Baltes | A61N 5/1071 |
| 10,964,429 | B2* | 3/2021 | Yaddanapudi | A61N 5/1075 |
| 11,090,512 | B2* | 8/2021 | Baltes | A61N 5/1031 |
| 11,393,582 | B2* | 7/2022 | Yaddanapudi | G16H 40/40 |
| 11,547,386 | B1* | 1/2023 | Roy | G01S 7/52038 |
| 11,600,004 | B2* | 3/2023 | Kapatoes | A61N 5/103 |
| 11,633,626 | B2* | 4/2023 | Voronenko | A61N 5/1065 378/65 |
| 11,648,418 | B2* | 5/2023 | Owens | A61N 5/1049 378/65 |
| 11,756,680 | B2* | 9/2023 | Yaddanapudi | A61N 5/1075 702/182 |
| 11,791,041 | B2* | 10/2023 | Yaddanapudi | A61N 5/1075 702/182 |
| 11,794,037 | B2* | 10/2023 | Ramezanzadeh Moghadam | G16H 20/40 |
| 11,896,848 | B2* | 2/2024 | Janardhanan | A61N 5/1039 |
| 12,216,234 | B2* | 2/2025 | Sumi | G01S 7/52041 |
| 2008/0083871 | A1* | 4/2008 | Cravens | A61N 5/1048 250/252.1 |
| 2010/0012829 | A1* | 1/2010 | Islam | G01T 1/2935 250/252.1 |
| 2011/0116684 | A1* | 5/2011 | Coffman | G06T 7/277 382/103 |
| 2013/0027040 | A1* | 1/2013 | Alagappan | A61B 6/4417 324/322 |
| 2013/0114784 | A1* | 5/2013 | Nioutsikou | A61N 5/1038 378/4 |
| 2014/0105355 | A1* | 4/2014 | Toimela | A61N 5/1064 382/132 |
| 2014/0336438 | A1* | 11/2014 | Bharat | A61N 5/1039 601/3 |
| 2015/0077118 | A1* | 3/2015 | Shvartsman | G01R 33/3858 324/322 |
| 2015/0224342 | A1* | 8/2015 | Baltes | A61N 5/1045 378/62 |
| 2016/0015357 | A1* | 1/2016 | Rozas | A61B 6/585 378/207 |
| 2016/0136460 | A1* | 5/2016 | Baltes | A61N 5/1071 378/165 |
| 2016/0146911 | A1 | 5/2016 | Chmielewski et al. | |
| 2016/0287906 | A1* | 10/2016 | Nord | A61N 5/103 |
| 2016/0361569 | A1* | 12/2016 | Sayeed | A61N 5/1038 |
| 2016/0361570 | A1* | 12/2016 | Sayeed | A61N 5/1039 |
| 2017/0184713 | A1* | 6/2017 | Robert | A61B 8/5269 |
| 2018/0310857 | A1* | 11/2018 | Pusa | G01R 33/34007 |
| 2019/0160308 | A1* | 5/2019 | Baltes | A61N 5/1031 |
| 2019/0192106 | A1* | 6/2019 | Rozas | A61B 6/585 |
| 2020/0238103 | A1* | 7/2020 | Baltes | A61N 5/1067 |
| 2022/0291318 | A1* | 9/2022 | Brown | A61N 5/1039 |
| 2023/0028022 | A1* | 1/2023 | Freedman | A61N 5/1071 |
| 2023/0110626 | A1* | 4/2023 | Broad | A61N 5/1045 378/65 |
| 2024/0241238 | A1* | 7/2024 | Sumi | G01S 15/8915 |
| 2025/0102523 | A1* | 3/2025 | Smith | G01N 33/6893 |

FOREIGN PATENT DOCUMENTS

| | | |
|---|---|---|
| WO | WO-2008013944 A2 | 1/2008 |
| WO | WO-2014133544 A1 | 9/2014 |

OTHER PUBLICATIONS

"International Application No. PCT/EP2020/086439, International Search Report dated Apr. 12, 2021", (Apr. 12, 2021), 4 pgs.

"International Application No. PCT/EP2020/086439, Written Opinion dated Apr. 12, 2021", (Apr. 12, 2021), 6 pgs.

Bawazeer, Omemh, et al., "A simple and efficient method to measure beam attenuation through a radiotherapy treatment couch and immobilization devices", Australasian Physical & Engineering Sciences in Medicine 42.4, (2019), pp. 1183-1189.

Li, Heng, et al., "Characterization of dose impact on IMRT and VMAT from couch attenuation for two Varian couches", Journal of applied clinical medical physics 12.3, (2011), pp. 23-31.

Torres-Xirau, Iban, et al., "Two-dimensional EPID dosimetry for an MR-linac: proof of concept", Medical Physics 46.9, (2019), pp. 4193-4203.

"Chinese Application No. 202080096954.0, Office Action dated Apr. 23, 2025", w English Translation, (Apr. 23, 2025), 10 pgs.

* cited by examiner

CHARACTERIZING PHYSICAL PROPERTIES OF AN ATTENUATING ELEMENT IN A RADIOTHERAPY DEVICE

PRIORITY APPLICATIONS

This application is a U.S. National Stage Filing under 35 U.S.C. § 371 from International Application No. PCT/EP2020/086439, filed on Dec. 16, 2020, and published as WO2021/122761 on Jun. 24, 2021, which claims the benefit of priority to United Kingdom Application No. 1918767.3, filed on Dec. 18, 2019; the benefit of priority of each of which is hereby claimed herein, and which applications and publication are hereby incorporated herein by reference in their entireties.

This disclosure relates to a method of characterising physical properties of an attenuating element in a radiotherapy device.

BACKGROUND

The present disclosure relates to a machine, apparatus or device for radiotherapy, and a method implemented in such a device. Radiotherapy devices are an important tool in modern cancer treatment. The device may be suitable for delivering a beam of radiation to a patient in order to treat a tumour. An example of a radiation source for producing a beam is a linear accelerator (LINAC). Clinical LINAC devices are configured to deliver high energy radiation to a patient.

Radiotherapy machines are becoming increasingly varied in design in order to provide different treatments in an effective manner. For example, the electron beam produced by the LINAC may itself be used for therapy or may be directed to a target that produces X-ray radiation to be used for therapy. Different LINAC designs may be used to produce radiation with differing properties.

Radiotherapy devices are large, complex machines, with many moving parts and inter-operating mechanisms, requiring precision engineering and rigorous testing. Some component parts of radiotherapy machines may interact with other component parts in complex ways. One such example is the attenuation of radiation caused by passing it through a cryostat, an integral part of some machines.

The Elekta-Unity MR-LINAC (magnetic resonance linear accelerator) is an example of a system that delivers radiation through a helium-filled cryostat. The LINAC component can provide radiotherapy and x-ray imaging capability. The MR component can provide magnetic resonance imaging capability. Typically, the radiation from the LINAC will be delivered through the cryostat of the MR apparatus. In such systems cryostat imperfections, e.g. metal plate thickness tolerances or weld seams, cause changes in radiation output with gantry rotation, with undesirable variation in beam attenuation. In general, the variations in attenuation occur in all directions but as the length of the arc (gantry rotation direction) is longer, so too is the variation. These changes in output are above typical specifications for the variation in dose output (the ratio of the set radiation dose to that measured at isocentre). Typically, the cryostat assembly produces variation of the output by less than 5%, with a typical specification of 1% required.

In known solutions, to compensate for cryostat inhomogeneity, Farmer chamber measurements can be employed to obtain the magnitude of the variations. In this technique, a radiation detector, such as a PTW Farmer Ionization Chamber, available from PTW Freiburg GmbH, is placed at the isocentre. The dose is measured every 2 degrees for a fixed monitor unit delivery. Farmer chamber measurements are both difficult and time consuming. Errors can be introduced due to air gaps, such as between a Perspex build up cap and the chamber, and costly equipment is required. Furthermore, when using a Farmer chamber, the attenuation is determined relative to a reference angle and is determined in an angular axis only for 1 cryostat shell. Such an approximation neglects any variation caused by divergence of the beam in a multi-shell cryostat, whereby a ray may pass through one layer at a certain angle and then through another layer at another angle.

SUMMARY

An invention is set out in the independent claims Optional features are set out in the dependent claims.

FIGURES

Specific embodiments are now described, by way of example only, with reference to the drawings, in which.

DETAILED DESCRIPTION

In overview, the present invention seeks to address the disadvantages encountered in the prior art by providing a method for determining the radiation attenuation through the cryostat. The present method provides an alternative solution to cryostat characterisation that is faster and less prone to error than Farmer chamber measurements. In one example, a series of images are acquired with an on-gantry imaging device, such as that of the Elekta-Unity system. This imager captures the radiation attenuation through two section passings of the cryostat (entry and exit). A fully automated imaging device-driven numerical model can be used to derive and account for perturbations in beam attenuation due to cryostat inhomogeneity. By acquiring multiple images over the 360 degree gantry range it is possible to determine the radiation attenuation through the cryostat. This information can then be supplied to a treatment planning system where the cryostat attenuation can be taken into account during dose calculation. For example, this can be done in software by performing a dose calculation in the treatment planning system that calculates the attenuation of individual photon rays as they pass through a suitable cryostat model, such as a transmission cylinder.

The suggested methodology mitigates the laborious and time-consuming task of measuring cryostat inhomogeneity using Farmer chamber measurements. The method can be integrated into an automated workflow. Although the suggested methodology measures radiation that has passed through two sections of the cryostat, the low average error between obtained perturbation coefficients indicates that the model well represents Farmer chamber measurements taken at the isocentre.

High-Level Overview of an MR-LINAC

Figure 1:
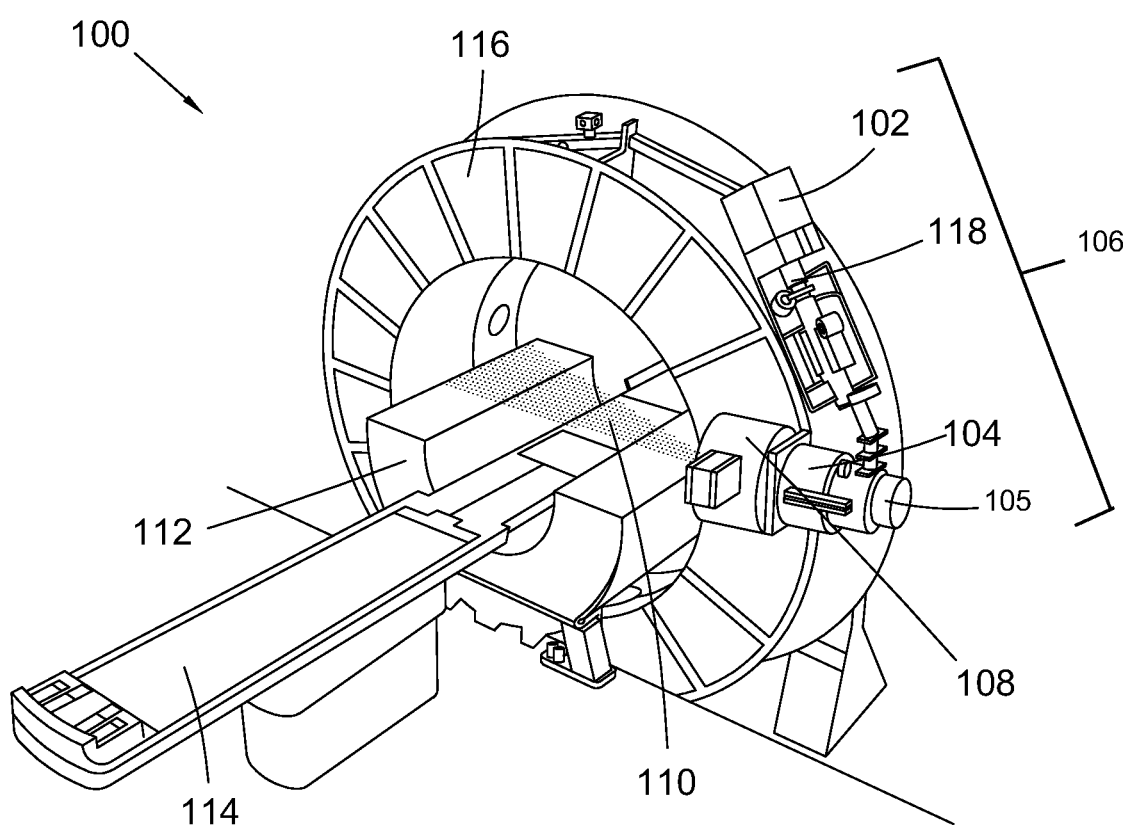
FIG. 1 is a schematic illustration of an MR-LINAC device.

FIG. 1 depicts a radiotherapy device 100 suitable for delivering, and configured to deliver, a beam of radiation to a patient during radiotherapy treatment. The device and its constituent components will be described generally for the purpose of providing useful accompanying information for the present invention. The device depicted in FIG. 1 is in accordance with the present disclosure and is suitable for use with the disclosed systems and apparatuses. While the device in FIG. 1 is an MR-LINAC, the implementations of the present disclosure may be any radiotherapy device, for example a LINAC device.

The device depicted in FIG. 1 is an MR-LINAC. The device comprises both MR imaging apparatus 112 and radiotherapy (RT) apparatus which may comprise a LINAC device. In operation, the MR scanner produces MR images of the patient, and the LINAC device produces and shapes a beam of radiation and directs it toward a target region within a patient's body in accordance with a radiotherapy treatment plan. The depicted device does not have the usual 'housing' which would cover the MR imaging apparatus 112 and RT apparatus in a commercial setting such as a hospital.

The MR-LINAC device 100 depicted in FIG. 1 comprises a source of radiation 106 which may comprise beam generation equipment, such as one or more of: a source of radiofrequency waves 102, a circulator 118, a source of electrons 105, a waveguide 104, and a target (not shown). The MR-LINAC device 100 may also comprise a collimator 108 such as a multi-leaf collimator configured to collimate and shape the beam, MR imaging apparatus 112, and a patient support surface 114. The device also comprises a housing which, together with the ring-shaped gantry defines a bore. The moveable support surface 114 can be used to move a patient, or other subject, into the bore when an MR scan and/or when radiotherapy is to commence. The MR imaging apparatus 112, RT apparatus, and a subject support surface actuator are communicatively coupled to a controller or processor. The controller is also communicatively coupled to a memory device comprising computer-executable instructions which may be executed by the controller.

The RT apparatus comprises a source of radiation 106 and a radiation detector (not shown). Typically, the radiation detector is positioned diametrically opposed to the radiation source 106. The radiation detector is suitable for, and configured to, produce radiation intensity data. In particular, the radiation detector is positioned and configured to detect the intensity of radiation which has passed through the subject. The radiation detector may also be described as radiation detecting means, and may form part of a portal imaging system.

The radiation source 106 defines the point at which the treatment beam 110 is introduced into the bore. The radiation source 106 forms part of a beam generation system, which may comprise a source of RF energy 102, an electron gun 105, and a waveguide 104. The beam generation system is attached to the rotatable gantry 116 so as to rotate with the gantry 116. In this way, the radiation source 106 is rotatable around the patient so that the treatment beam 110 can be applied from different angles around the gantry 116. In a preferred implementation, the gantry is continuously rotatable. In other words, the gantry can be rotated by 360 degrees around the patient, and in fact can continue to be rotated past 360 degrees. The gantry may be ring-shaped. In other words, the gantry may be a ring-gantry.

The source 102 of radiofrequency waves, such as a magnetron, is configured to produce radiofrequency waves. The source 102 of radiofrequency waves is coupled to the waveguide 104 via circulator 118, and is configured to pulse radiofrequency waves into the waveguide 104. Radiofrequency waves may pass from the source 102 of radiofrequency waves through an RF input window and into an RF input connecting pipe or tube. A source of electrons 105, such as an electron gun, is also coupled to the waveguide 104 and is configured to inject electrons into the waveguide 104. In the source of electrons, electrons are thermionically emitted from a cathode filament as the filament is heated. The temperature of the filament controls the number of electrons injected. The number of electrons injected may additionally be controlled by a gate voltage. The injection of electrons into the waveguide 104 is synchronised with the pumping of the radiofrequency waves into the waveguide 104. The design and operation of the radiofrequency wave source 102, electron source 105 and the waveguide 104 is such that the radiofrequency waves accelerate the electrons to very high energies as the electrons propagate through the waveguide 104.

The design of the waveguide 104 depends on whether the LINAC accelerates the electrons using a standing wave or travelling wave, though the waveguide typically comprises a series of cells or cavities, each cavity connected by a hole or 'iris' through which the electron beam may pass. The cavities are coupled in order that a suitable electric field pattern is produced which accelerates electrons propagating through the waveguide 104.

To ensure that propagation of the electrons is not impeded as the electron beam travels toward the target, the waveguide 104 is evacuated. Electrons can be accelerated to speeds approaching the speed of light in the evacuated waveguide 104.

The source of radiation 106 is configured to direct a beam 110 of therapeutic radiation toward a patient positioned on the patient support surface 114. The source of radiation 106 may comprise a heavy metal target toward which the high energy electrons exiting the waveguide are directed. When the electrons strike the target, X-rays are produced in a variety of directions. A primary collimator may block X-rays travelling in certain directions and pass only forward travelling X-rays to produce a treatment beam 110. The X-rays may be filtered and may pass through one or more ion chambers for dose measuring. The beam can be shaped in various ways by beam-shaping apparatus, for example by using a multi-leaf collimator 108, before it passes into the patient as part of radiotherapy treatment.

In some implementations, the source of radiation 106 is configured to emit either an X-ray beam or an electron particle beam. Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by adjusting the components of the LINAC.

The subject or patient support surface 114 is configured to move between a first position substantially outside the bore, and a second position substantially inside the bore. In the first position, a patient or subject can mount the patient support surface. The support surface 114, and patient, can then be moved inside the bore, to the second position, in order for the patient to be imaged by the MR imaging apparatus 112 and/or imaged or treated using the RT apparatus. The movement of the patient support surface is effected and controlled by a subject support surface actuator, which may be described as an actuation mechanism. The actuation mechanism is configured to move the subject support surface in a direction parallel to, and defined by, the central axis of the bore. The terms subject and patient are used interchangeably herein such that the subject support surface can also be described as a patient support surface. The subject support surface may also be referred to as a moveable or adjustable couch or table.

The radiotherapy apparatus/device depicted in FIG. 1 also comprises MR imaging apparatus 112. The MR imaging apparatus 112 is configured to obtain images of a subject positioned, i.e. located, on the subject support surface 114. The MR imaging apparatus 112 may also be referred to as the MR imager. The MR imaging apparatus 112 may be a conventional MR imaging apparatus operating in a known manner to obtain MR data, for example MR images. The skilled person will appreciate that such a MR imaging apparatus 112 may comprise a primary magnet, one or more gradient coils, one or more receive coils, and an RF pulse applicator. The operation of the MR imaging apparatus is controlled by the controller.

The controller is a computer, processor, or other processing apparatus. The controller may be formed by several discrete processors; for example, the controller may comprise an MR imaging apparatus processor, which controls the MR imaging apparatus 112; an RT apparatus processor, which controls the operation of the RT apparatus; and a subject support surface processor which controls the operation and actuation of the subject support surface. The controller is communicatively coupled to a memory, i.e. a computer readable medium.

As is well known to the skilled person, the LINAC device also comprises several other components and systems. The whole system is cooled by a water cooling system (not shown in the figures). The water cooling system may be used, in particular, to cool the waveguide 104, target, and radiofrequency source 102. In order to ensure the LINAC does not leak radiation, appropriate shielding is also provided. As will be understood by the person skilled in the art, a LINAC device used for radiotherapy treatment will have additional apparatus such as a gantry to support and rotate the LINAC, a patient support surface, and a controller or processor configured to control the LINAC apparatus.

Figure 2A:
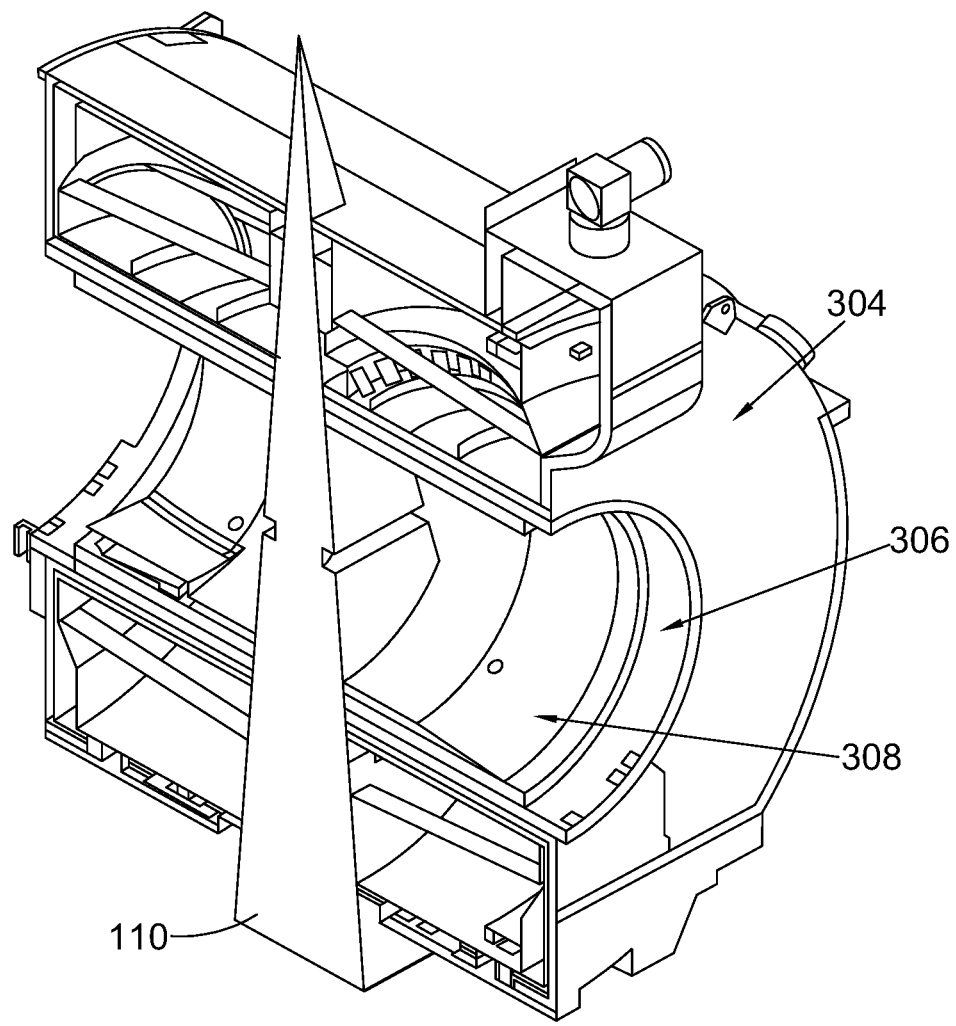
FIGS. 2A and 2B depict cross-sections of a cryostat.
Figure 2B:
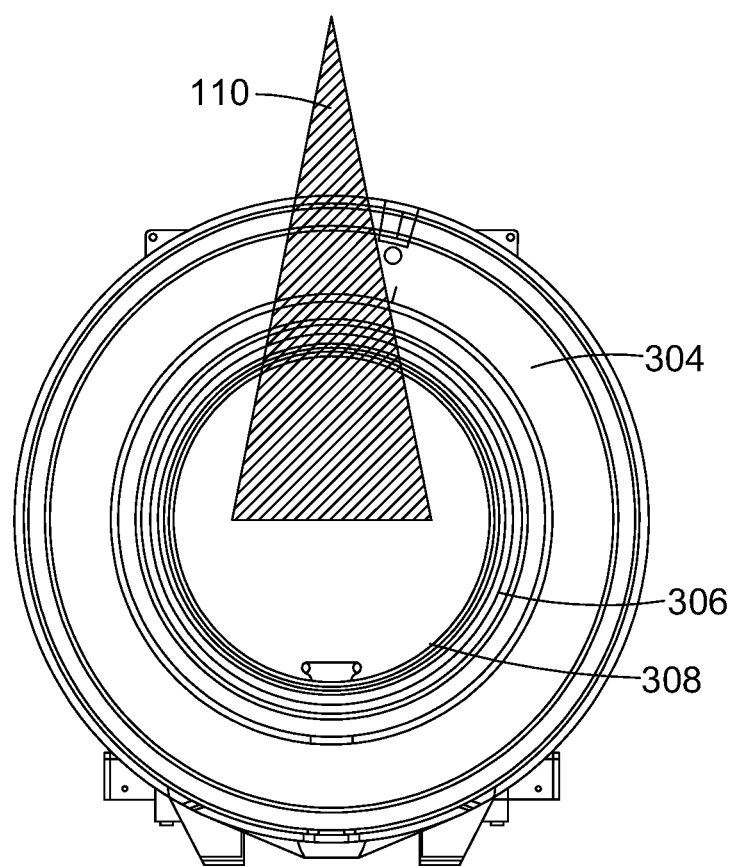

The LINAC component of the MR-LINAC device can provide radiotherapy and x-ray imaging capability. The MR component can provide magnetic resonance imaging capability. FIG. 2A and FIG. 2B. depict an example cross-section of a cryostat in a radiotherapy device. Typically, the radiation from the LINAC will be delivered through a field generation unit of the MR apparatus Radiation beam 110 is passed through a cryostat 304, gradient coil 306, and system body coil 308 before being delivered to a patient encircled by the device. The system body coil 308 may be a quadrature body coil. As used herein, the general term 'cryostat' may be used to refer to the overall field generation unit comprising cryostat 304, gradient body coil 306, and system body coil 308, any other appropriate refrigerant unit, or any other attenuating element. The cryostat may be toroidal or cylindrical and surround the patient during treatment. The cryostat may be fixed in position, with the gantry encircling the cryostat and providing a means for the LINAC to rotate 360 degrees to deliver radiation from different angles. Such an arrangement means that at any given position, radiation 110 will be delivered to the patient by passing it through the cryostat.

The gantry may also feature a radiation detector in the form of an imaging device, which may be positioned at the opposite point of the gantry diameter to radiation beam 110 and can be used to image the therapeutic radiation produced by the LINAC during radiotherapy treatment. The device may be a digital imaging device such as a CCD camera, other semiconductor-based detector, and/or liquid ion chamber. The device may be a megavoltage X-ray imager and/or an electronic portal imaging device (EPID). The device may comprise a flat panel detector, a scintillator, an a-Si based image panel, and/or a scintillator-mirror-camera system. References to EPID-based methods and apparatus within this disclosure should be considered to also apply to megavoltage X-ray imaging devices or any other appropriate imaging device.

Imaging Device-Driven Numerical Model

The approach described permits cryostat perturbations to be modelled numerically using existing imaging devices external to the chamber, such as megavoltage X-ray imaging devices and/or EPIDs, or any other suitable imaging device. Perturbations in beam attenuation due to cryostat inhomogeneity can be compensated by a fully automated imaging device-driven numerical model. Perturbations can be obtained from images using an appropriate geometrical representation of the cryostat. The chamber can be modelled as shown in FIG. 3A and FIG. 3B.

Figure 3A:
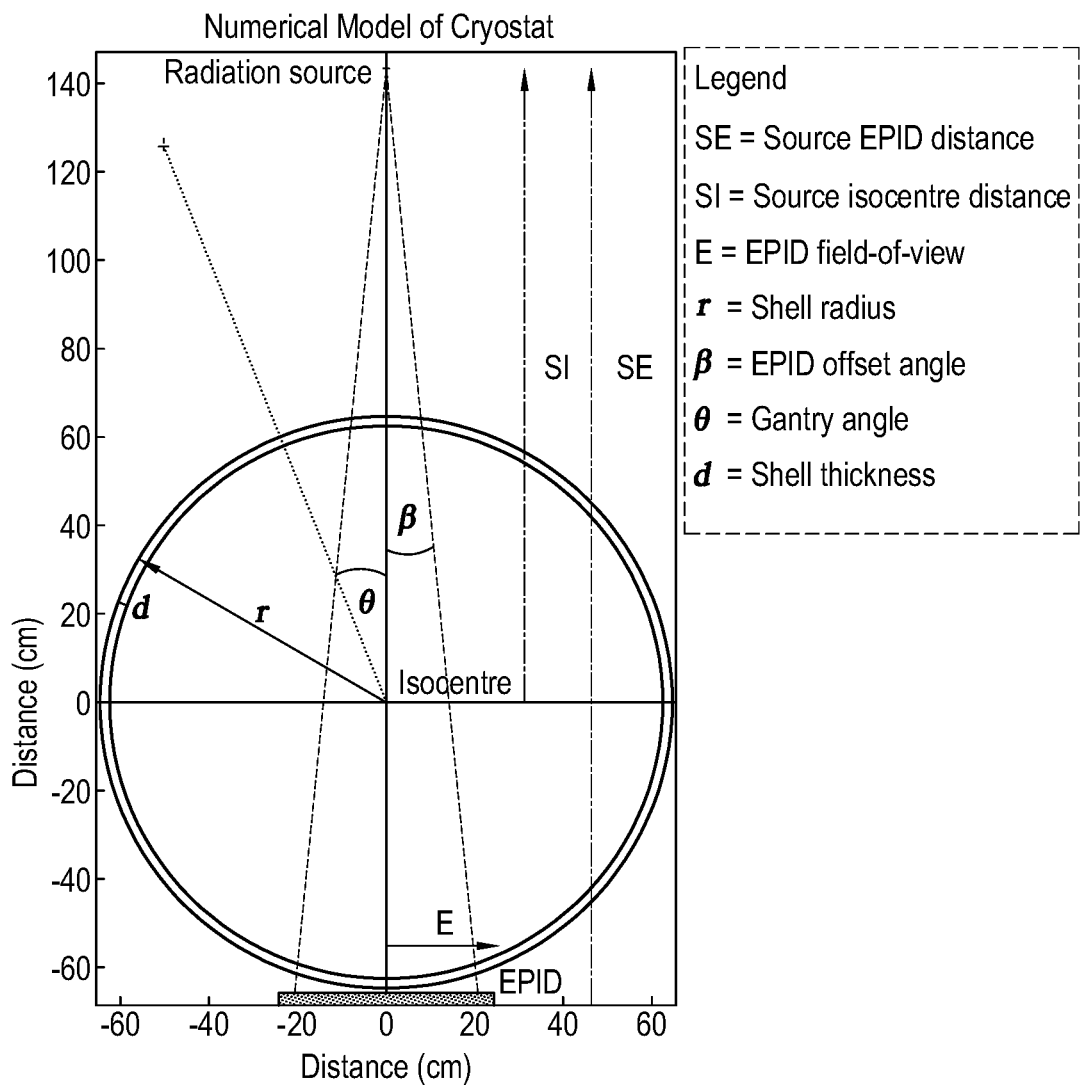
FIGS. 3A and 3B depict geometrical representations of relevant characteristics of the cryostat.

FIG. 3A depicts a schematic of the geometrical layout of the device considered by the model. In this example, the cryostat is modelled using a single shell with radius r and thickness d. A radiation source (solid cross) is placed at a distance SI from the isocentre. The source can rotate around the gantry by an angle $\theta$ and deliver beams at angle $\beta$ with respect to the central-axis. The radiation beams (dashed lines) intersect the shell (solid black circles) and the EPID (hatched rectangle) at a vertical distance SE (cm) from the radiation source and horizontal distance E (cm) from the isocentre. A radiation beam can be considered as a divergent beam comprising multiple beamlets radiating outwards from the source, including a central-axis beamlet and additional beamlets following respective paths forming a range of angles either side of the central axis.

Figure 3B:
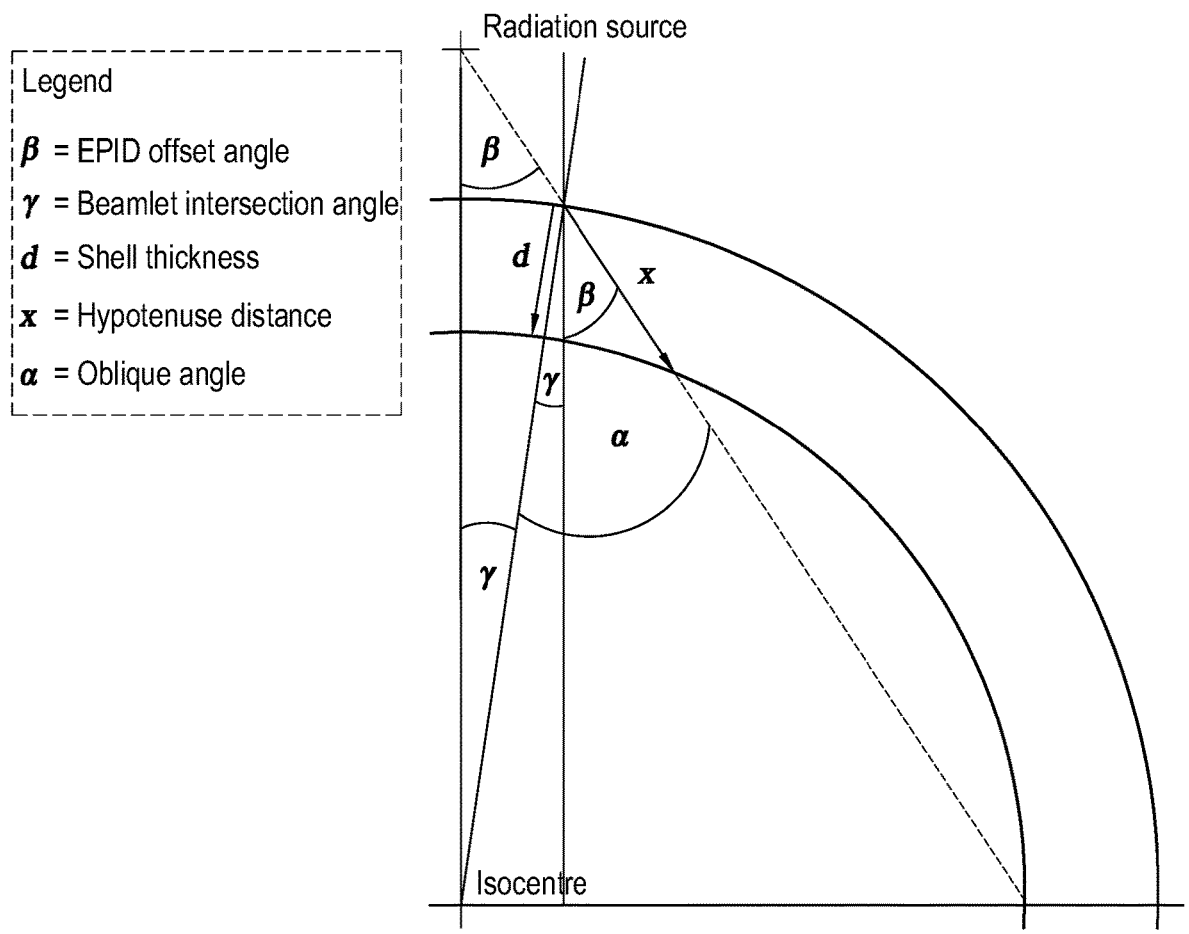

FIG. 3B depicts a zoom-in of the cryostat schematic. For beamlets delivered at an offset angle $\beta$ with respect to the central-axis, the distance x traversed by the beamlet through the cryostat can be approximately calculated using the oblique angle $\alpha$ and shell thickness d. The oblique angle $\alpha$ represents the angle between the beamlet path and a line from the isocentre that is perpendicular to the circumference of the cryostat; it can be obtained by summing $\beta$ and the beamlet intersection angle $\gamma$.

A beam passing through an attenuating material, such as a cryostat, will have its initial intensity $A_0$ attenuated to a value A. On an MR-LINAC, beamlets with incident intensity $A_0$, are delivered at gantry angles $\theta$ through a cryostat on both entry ($\theta_{Entry}$) and exit ($\theta_{Exit}$), passing through two sections of cryostat. The cryostat can be modelled as N aggregated shells, where the $k^{th}$ shell exhibits linear attenuation coefficient $\mu^k(\theta)$ and thickness $d^k(\theta)$. Beamlet attenuation can be modelled differently depending on whether they are oblique (they intersect the circumference of the cryostat at non-orthogonal angles) or non-oblique (they intersect the circumference of the cryostat at orthogonal angles). For non-oblique orthogonal beamlets, the intensity A ($\theta$) measured by an on-gantry EPID can be expressed as:

$$A(\theta) = A_0 \prod_{k=1}^{N} e^{-[\mu^k(\theta_{Entry})d^k(\theta_{Entry}) + \mu^k(\theta_{Exit})d^k(\theta_{Exit})]} \quad (1)$$

For oblique beamlets at angle $\alpha$, as shown in FIG. 3B, the local distance $x^k(\theta)$ traversed through the $k^{th}$ shell must be taken into account and for thin shells is given by:

$$x^k(\theta, \alpha) = d^k(\theta)/\cos(\alpha^k) \quad (2)$$

Using this, the intensity $A_p$ of an oblique beamlet passing through a perfectly homogeneous cryostat can be written as:

$$A_p(\theta, \alpha) = A_0 \prod_{k=1}^{N} e^{-\frac{1}{\cos(\alpha^k)}\left[\mu^k(\theta_{Entry}^k)d^k(\theta_{Entry}^k)+\mu^k(\theta_{Exit}^k)d^k(\theta_{Exit}^k)\right]} \quad (3)$$

Equations (1) and (3) can be used to model the intensity of either non-oblique or oblique beamlets measured by an on-gantry EPID.

If it is not possible to sample all gantry angles, each term in the above exponent can be linearly interpolated between the two nearest available gantry angles ($\theta_1^k < \theta_{Entry}^k < \theta_2^k$; $\theta_3^k < \theta_{Exit}^k < \theta_4^k$). $\lambda_{1-4}^k$ represent the interpolation factors for the entry and exit angles in and out of the $k^{th}$ shell:

$$\lambda_{1-4}^k = \frac{\theta_2^k - \theta_{Entry}^k}{\theta_2^k - \theta_1^k}, \lambda_2^k = 1 - \lambda_1^k, \lambda_3^k = \frac{\theta_4^k - \theta_{Exit}^k}{\theta_4^k - \theta_3^k}, \lambda_4^k = 1 - \lambda_3^k \quad (4)$$

Interpolation factors $\lambda$ and oblique cosine factors $\cos(\alpha^k)$ can be obtained by simulating the beamlet paths through the cryostat using ray-tracing. First, beamlet intersections ($x^k$, $y^k$) with the $k^{th}$ cryostat shell at gantry angle $\theta=0$ are found by solving the following simultaneous equations (FIG. 3A):

$$y^k = -\frac{SE}{E}x^k + SI \quad (5)$$

$$(r^k)^2 = (x^k)^2 + (y^k)^2 \quad (6)$$

Where SE, E, SI and $r^k$ are the source EPID distance, EPID field-of-view, source isocentre distance and radius of the $k^{th}$ cryostat shell respectively.

The two solutions correspond to the beamlet entry and exit:

$$y^k = \frac{SI\left[\frac{E}{SE}\right]^2 \pm \sqrt{SI^2\left[\frac{E}{SE}\right]^4 - \left(1+\left[\frac{E}{SE}\right]^2\right)\left(SI^2\left[\frac{E}{SE}\right]^2 - (r^k)^2\right)}}{\left(1+\left[\frac{E}{SE}\right]^2\right)} \quad (7)$$

$$x^k = (SI - y^k)\left[\frac{E}{SE}\right] \quad (8)$$

Using the information in FIG. 3B, the two solutions above can be used to calculate the beamlet intersection angles on entry and exit, $\gamma_{Entry}^k$ and $\gamma_{Exit}^k$, as:

$$\gamma_{Entry/Exit}^k = \tan^{-1}\left(\frac{x^k}{y^k}\right) \quad (9)$$

Then the oblique incidence cosine on entry and on exit is:

$$\cos(\alpha^k) = \cos(\gamma_{Entry}^k + \beta) = \cos\left(\tan^{-1}\left(\frac{x^k}{y^k}\right) + \tan^{-1}\left(\frac{E}{SE}\right)\right) \quad (10)$$

Where $\beta$ is the EPID offset angle. Oblique cosines calculated for gantry angle $\theta=0$ can be valid for all other gantry angles. Interpolation factors $\lambda_{1-4}^k$ can be determined from the beam intersections $\gamma^k$ at gantry angle $\theta=0$. First, the beam intersection angles at arbitrary gantry angles $\theta$ can be determined as:

$$\theta_{Entry}^k = \gamma_{Entry}^k + \theta \quad (11)$$

$$\theta_{Exit}^k = \gamma_{Exit}^k + \theta \quad (12)$$

Interpolation factors $\lambda_{1-4}^k$ for each gantry angle can then be computed as weightings between the two closest available angles, such that:

$$\theta_{Entry}^k = \lambda_1^k \theta_1^k + \lambda_2^k \theta_2^k \quad (13)$$

$$\theta_{Exit}^k = \lambda_3^k \theta_3^k + \lambda_4^k \theta_4^k \quad (14)$$

Using the calculated interpolation factors and oblique cosines the perturbations for one shell can be calculated using a sparse linear matrix solver.

Defining $\delta^k(\theta) = \mu^k(\theta)d^k(\theta)$ and using equations (4), equation (3) can be rewritten as:

$$A_p(\theta, \alpha) = \quad (15)$$

$$A_0 \prod_{k=1}^{N} e^{-\frac{1}{\cos(\alpha^k)}\left[\lambda_1^k \mu^k(\theta_1^k)d^k(\theta_1^k)+\lambda_2^k \mu^k(\theta_2^k)d^k(\theta_2^k)+\lambda_3^k \mu^k(\theta_3^k)d^k(\theta_3^k)+\lambda_4^k \mu^k(\theta_4^k)d^k(\theta_4^k)\right]}$$

$$\equiv A_0 \prod_{k=1}^{N} e^{-\frac{1}{\cos(\alpha^k)}\left[\lambda_1^k \delta^k(\theta_1^k)+\lambda_2^k \delta^k(\theta_2^k)+\lambda_3^k \delta^k(\theta_3^k)+\lambda_4^k \delta^k(\theta_4^k)\right]} \quad (16)$$

Equations (15) and (16) describe the attenuation of a radiation beam by an idealised, homogeneous cryostat. In order to consider the effect of cryostat imperfections, the beamlet intensity as attenuated by inhomogeneities in d, $\mu$, or both, can be approximated with first order perturbations $\varepsilon$ in $\delta$:

$$A_{p+\varepsilon}(\theta, \alpha) = A_p(\theta, \alpha) \prod_{k=1}^{N} e^{-\frac{1}{\cos(\alpha^k)}\left[\lambda_1^k \varepsilon^k(\theta_1^k)+\lambda_2^k \varepsilon^k(\theta_2^k)+\lambda_3^k \varepsilon^k(\theta_3^k)+\lambda_4^k \varepsilon^k(\theta_4^k)\right]} \quad (17)$$

Although localised inhomogeneities will cause perturbations in the attenuation, the cryostat attenuation as a whole can be approximated as a homogeneous average of the effect of those perturbations. $A_p(\theta, \alpha)$ can be approximated by the median beamlet intensity over all gantry angles from 0 to 360 degrees (or $2\pi$ radians).

$$A_p(\theta, \alpha) \approx \langle A_{p+\varepsilon}(\theta, \alpha) \rangle_{\theta \in [0:2\pi]} \quad (18)$$

This allows for the calculation of the perturbated beam intensity $R(\theta, \alpha)$ seen at the EPID as the ratio of the intensity detected at a given $\theta$ and $\alpha$ to the median beamlet intensity detected over all gantry angles at a given $\alpha$:

$$R(\theta, \alpha) = \quad (19)$$

$$\frac{A_{p+\varepsilon}}{\langle A_{p+\varepsilon}\rangle_{\theta \in [0:2\pi]}} \approx \prod_{k=1}^{N} e^{-\frac{1}{\cos(\alpha^k)}\left[\lambda_1^k \varepsilon^k(\theta_1^k)+\lambda_2^k \varepsilon^k(\theta_2^k)+\lambda_3^k \varepsilon^k(\theta_3^k)+\lambda_4^k \varepsilon^k(\theta_4^k)\right]}$$

The perturbated beam intensity R can be experimentally obtained from an EPID image E as the ratio of the intensity detected at a given θ and α to the median beamlet intensity detected over all gantry angles at a given α:

$$R(\theta, \alpha) \approx \frac{E(\theta, \alpha)}{\langle E(\theta, \alpha)\rangle_{\theta \in [0: 2\pi]}} \quad (20)$$

Where, again, $\langle E(\theta, \alpha)\rangle_{\theta \in [0:2\pi]}$ is the median EPID image value over the full range of gantry angles. In equation (20) it is assumed that E(θ, α) is proportional to $A_{p+\epsilon}$ with some constant factors, such as detector efficiency, and that those factors cancel out when the ratio is calculated.

If the perturbations are small, a Maclaurin expansion can be applied to R(θ, α):

$$R(\theta, \alpha) \approx \prod_{k=1}^{N} \left(1 - \frac{1}{\cos(\alpha^k)}\left[\lambda_1^k \varepsilon^k(\theta_1^k) + \lambda_2^k \varepsilon^k(\theta_2^k) + \lambda_3^k \varepsilon^k(\theta_3^k) + \lambda_4^k \varepsilon^k(\theta_4^k)\right]\right) \quad (21)$$

Then, for one shell (N=1), the product reduces to one factor and the index k can be dropped. The perturbation coefficients ε can be calculated using:

$$1 - \frac{E(\theta, \alpha)}{\langle E\rangle_{\theta \in [0: 2\pi]}} \approx \frac{1}{\cos(\alpha^1)}[\lambda_1 \varepsilon(\theta_1) + \lambda_2 \varepsilon(\theta_2) + \lambda_3 \varepsilon(\theta_3) + \lambda_4 \varepsilon(\theta_4)] \quad (22)$$

For many shells the perturbation coefficients $\varepsilon^k$ are calculated similarly from:

$$1 - \frac{E(\theta, \alpha)}{\langle E\rangle_{\theta \in [0: 2\pi]}} \approx \quad (23)$$

$$\sum_{k=1}^{N} \frac{1}{\cos(\alpha^k)}\left[\lambda_1^k \varepsilon^k(\theta_1^k) + \lambda_2^k \varepsilon^k(\theta_2^k) + \lambda_3^k \varepsilon^k(\theta_3^k) + \lambda_4^k \varepsilon^k(\theta_4^k)\right]$$

As shown in FIG. 3A, a perturbated beam intensity R calculated from an EPID image will have been attenuated by two sections of the cryostat, whereas the attenuated beam intensity at the isocentre is the quantity of interest for treatment planning By using equations (22) or (23) with the experimental EPID image values of equation (20), perturbation coefficients can be calculated. Those perturbation coefficients can be used with equation (17), modified to account for only one cryostat section passing, to calculate the beam attenuation due to the cryostat at the isocentre. For the isocentre beamlet the incidence through all the shells is normal, thus all cosine factors are 1, and the angles $\theta_1^k$ and $\theta_2^k$ and the interpolation coefficients $\lambda_1^k$ and $\lambda_1^k$ do not depend on the shell radius or on the index k. Thus equation 17 simplifies to:

$$A_{isocentre}(\theta, \alpha) = A_0 \prod_{k=1}^{N} e^{-[\lambda_1 \mu^k(\theta_1)d^k(\theta_1)\varepsilon^k(\theta_1)+\lambda_2 \mu^k(\theta_2)d^k(\theta_2)\varepsilon^k(\theta_2)]} \quad (24)$$

This value can then be used to fully characterise the cryostat and enable the intensity of radiation beam 110 to be adjusted accordingly to compensate for cryostat inhomogeneities.

Adjusting the beam intensity to compensate for cryostat inhomogeneities may be done during a device calibration phase or done in real-time during treatment. This will offer an improvement from the common variation of the output by less than 5%, allowing a treatment plan to better achieve the required specification of 1%. The reduction of variation can be verified by implementing cryostat inhomogeneity compensation in the treatment planning system, using the treatment planning system to deliver a fixed dose to isocentre and confirming that a fixed dose is measured at isocentre.

Figure 4:
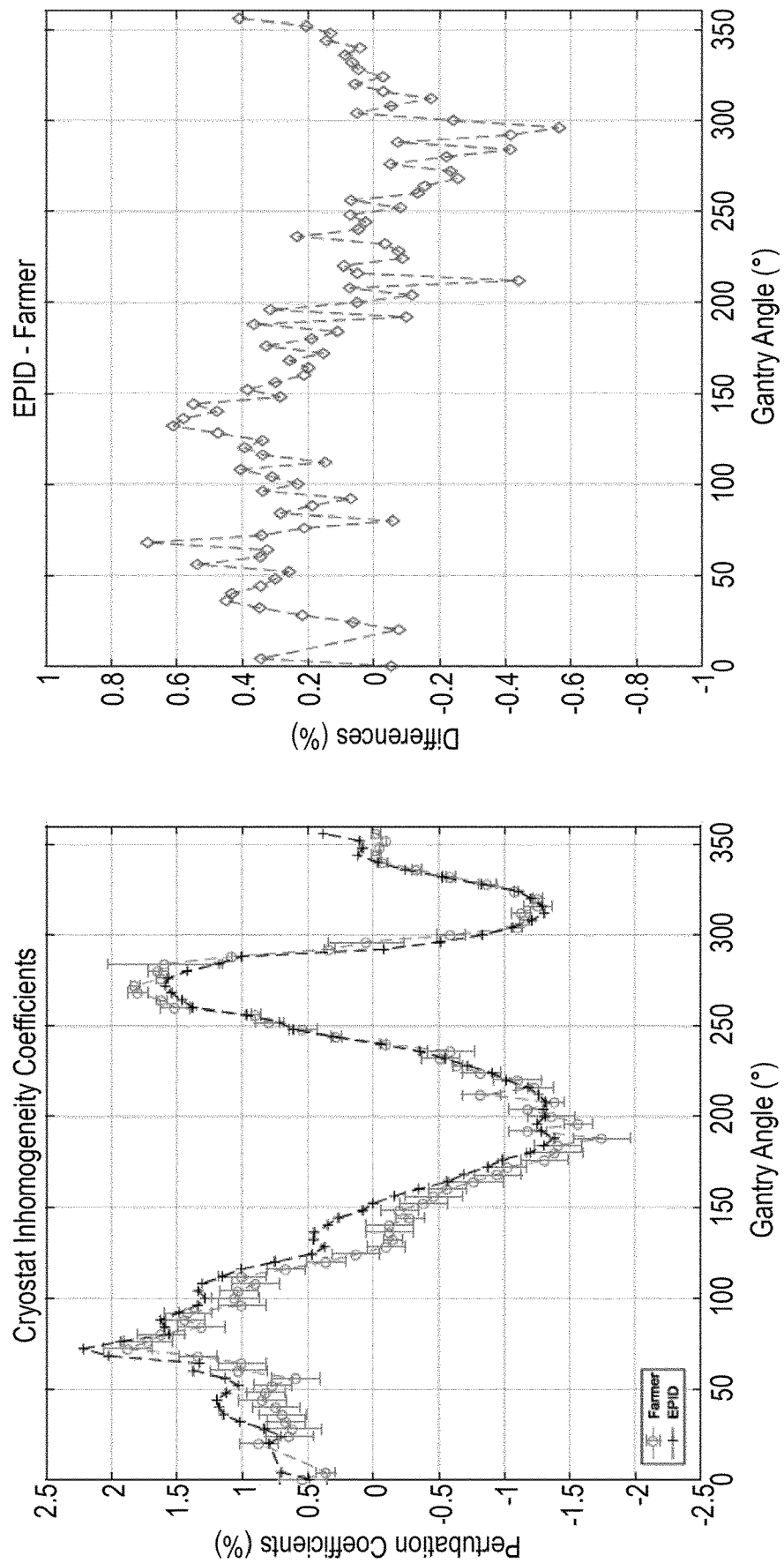
FIG. 4 depicts a comparison of experimental data characterising a cryostat according to the present disclosure with Farmer-chamber measurement data.

FIG. 4 depicts a comparison of the results of the present method with the results of more time-consuming Farmer-chamber measurements. A very close match between the present method and the slower conventional measurement technique is observed.

A Farmer-chamber was employed to validate the calculated perturbations. Charge measured by a Farmer chamber C(θ), placed at the system isocentre, using non-oblique beamlets can be written as:

$$C(\theta) \propto \Sigma_{k=1}{}^N e^{-\mu^k(\theta)x^k(\theta)} \quad (25)$$

Following the same logic as per the EPID measurements, the perturbation coefficients can be expressed as:

$$1 - \frac{C(\theta)}{\langle C \rangle_{\theta \in [0: 2\pi]}} \approx \varepsilon(\theta) \quad (26)$$

Good agreement was obtained between the perturbation coefficients calculated from the EPID-driven numerical model and the ground-truth Farmer-chamber measurements (depicted in FIG. 4). The mean and standard deviation error (over all gantry angles) of the absolute differences between the EPID and Farmer-chamber perturbation coefficients were Wide-beam: 0.23±0.16%; Thin-beam: 0.20±0.18%. Perturbation coefficients were calculated in approximately 25 seconds on an Intel i7-3540M processor with 8 GB of RAM, providing a surprisingly fast, accurate characterisation technique.

The present method provides an alternative solution to cryostat characterisation that is faster and less prone to error than Farmer chamber measurements. A negligible discrepancy is observed between the present method and slower Farmer chamber attenuation measurements. The present method provides a means to take into account variation in the Y direction (and possibly anomalies) and to take into account different cryostat layers. Due to the ease of use of the method, it could allow for user cryostat characterization to take into account the helium level of the cryostat.

The present method may also be used to correct for changes in beam symmetry as the radiation source is rotated around the gantry. The present method may be implemented using an imaging device placed either inside or outside the cryostat. The present method may be implemented using kilovolt (kV) energy x-rays and/or megavolt (mV) energy x-rays, with the imaging device chosen appropriately.

The present method may be implemented on an apparatus or system configured to perform the steps outlined above. The present method may be performed by a processor that is arranged to execute instructions stored in a computer-readable medium, the instructions causing the processor to perform the disclosed method.

The invention claimed is:

1. A method of characterizing physical properties of an attenuating element in a radiotherapy device including a radiotherapy radiation source located on a first side of the attenuating element and a radiotherapy radiation detector located on a second side of the attenuating element, wherein the attenuating element comprises a cylindrical component, and wherein the cylindrical component comprises one of a cryostat, a gradient coil, or a quadrature body coil, the method comprising:

obtaining an average detected radiotherapy radiation intensity at two or more locations around the attenuating element;

comparing a detected intensity at one location with the average radiotherapy radiation intensity; and characterizing a corresponding physical property based on the comparison, wherein the characterized physical property is at least one perturbation coefficient given by the equation:

$$1 - \frac{E(\theta, \alpha)}{\langle E \rangle_{\theta \in [0: 2\pi]}} \approx \frac{1}{\cos(\alpha^1)} \left[ \lambda_1^1 \varepsilon^1(\theta_1) + \lambda_2^1 \varepsilon^1(\theta_2) + \lambda_3^1 \varepsilon^1(\theta_3) + \lambda_4^1 \varepsilon^1(\theta_4) \right],$$

and wherein $$\frac{E(\theta, \alpha)}{\langle E \rangle_{\theta \in [0: 2\pi]}}$$

is derived from comparing the detected intensity at one location with the average intensity.

2. The method of claim 1, wherein the radiotherapy radiation source comprises a linear accelerator.

3. The method of claim 1, wherein the radiotherapy radiation detector is rotatable in relation to the attenuating element, and wherein the corresponding physical property relates to a rotary angle.

4. The method of claim 1, wherein the radiotherapy radiation source is located diametrically opposite the radiotherapy radiation detector.

5. The method of claim 1, further comprising:
using the characterized physical property to calibrate or control the radiation intensity.

6. The method of claim 1, wherein the method is performed to calibrate the radiotherapy device.

7. A method of controlling operation of a radiotherapy device comprising a radiotherapy radiation source on a first side of an attenuating element and a radiotherapy radiation detector on a second side of the attenuating element, wherein the attenuating element comprises a cylindrical component, and wherein the cylindrical component comprises one of a cryostat, a gradient coil, or a quadrature body coil, the method comprising:

delivering radiation from the radiotherapy radiation source to an isocentre; and characterizing at least one aspect of radiation attenuation using the radiotherapy radiation detector, wherein the characterizing includes:

obtaining an average detected radiotherapy radiation intensity at two or more locations around the attenuating element;

comparing a detected intensity at one location with the average detected radiotherapy radiation intensity; and characterizing a corresponding physical property based on the comparison, wherein the characterized physical property is at least one perturbation coefficient given by the equation:

$$1 - \frac{E(\theta, \alpha)}{\langle E \rangle_{\theta \in [0: 2\pi]}}$$

and wherein $$1 - \frac{E(\theta, \alpha)}{\langle E \rangle_{\theta \in [0: 2\pi]}} \approx \frac{1}{\cos(\alpha^1)} \left[ \lambda_1^1 \varepsilon^1(\theta_1) + \lambda_2^1 \varepsilon^1(\theta_2) + \lambda_3^1 \varepsilon^1(\theta_3) + \lambda_4^1 \varepsilon^1(\theta_4) \right],$$

is derived from comparing the detected intensity at one location with the average intensity.

8. The method of claim 7, further comprising:
correcting an intensity of radiation being delivered to the isocentre in accordance with the at least one aspect of radiation attenuation.

9. The method of claim 8, wherein the characterization and correcting are performed in real-time during radiation delivery.

10. The method of claim 8, wherein the correcting is performed after a calibration procedure comprising the characterizing step.

11. A radiotherapy apparatus comprising:

an attenuating element, wherein the attenuating element comprises a cylindrical component, and wherein the cylindrical component comprises one of a cryostat, a gradient coil, or a quadrature body coil;

a radiotherapy radiation source located on a first side of the attenuating element;

a radiotherapy radiation detector on a second side of the attenuating element;

a processor; and memory, including instructions stored thereon, which when executed by the processor cause the processor to perform operations, the operations comprising:

obtaining an average detected radiotherapy radiation intensity at two or more locations around the attenuating element;

comparing a detected intensity at one location with the average detected radiotherapy radiation intensity; and characterizing a corresponding physical property based on the comparison, wherein the characterized physical property is at least one perturbation coefficient given by the equation:

$$1 - \frac{E(\theta, \alpha)}{<E>_{\theta \in [0:2\pi]}} \approx \frac{1}{\cos(\alpha^1)} \left[ \lambda_1^1 \varepsilon^1(\theta_1) + \lambda_2^1 \varepsilon^1(\theta_2) + \lambda_3^1 \varepsilon^1(\theta_3) + \lambda_4^1 \varepsilon^1(\theta_4) \right],$$

and wherein $$\frac{E(\theta, \alpha)}{<E>_{\theta \in [0:2\pi]}}$$

is derived from comparing the detected intensity at one location with the average intensity.

12. The radiotherapy apparatus of claim 11, wherein the radiation detector is rotatable with respect to the attenuating element, and wherein the corresponding physical property relates to a rotary angle of the radiation detector.

13. The radiotherapy apparatus of claim 11, wherein the first side of the attenuating element containing the radiotherapy radiation source is located diametrically opposite to the second side of the attenuating element containing the radiotherapy radiation detector.

14. A non-transitory computer-readable medium containing instructions which, when executed by a processor, causes the processor to:
    obtain an average detected radiotherapy radiation intensity at two or more locations around an attenuating element included in a radiotherapy device, wherein the attenuating element comprises a cylindrical component, and wherein the cylindrical component comprises one of a cryostat, a gradient coil, or a quadrature body coil;
    compare a detected intensity at one location with the average detected radiotherapy radiation intensity;
    characterize a corresponding physical property based on the comparison, wherein the characterized physical property is at least one perturbation coefficient given by the $$1 - \frac{E(\theta, \alpha)}{<E>_{\theta \in [0:2\pi]}} \approx \frac{1}{\cos(\alpha^1)} \left[ \lambda_1^1 \varepsilon^1(\theta_1) + \lambda_2^1 \varepsilon^1(\theta_2) + \lambda_3^1 \varepsilon^1(\theta_3) + \lambda_4^1 \varepsilon^1(\theta_4) \right],$$

and wherein $$\frac{E(\theta, \alpha)}{<E>_{\theta \in [0:2\pi]}}$$

is derived from comparing the detected intensity at one location with the average intensity; and
    use the characterized physical property to at least one of calibrate or control the radiation intensity.

15. The non-transitory computer-readable medium of claim 14, wherein the radiotherapy device includes a radiation source, and wherein the radiotherapy radiation source comprises a linear accelerator.

16. The non-transitory computer-readable medium of claim 14, wherein the processor is further to:
    calibrate the radiotherapy device.

* * * * *